United States Patent
Kerr et al.

(10) Patent No.: US 10,022,094 B2
(45) Date of Patent: Jul. 17, 2018

(54) X-RAY DISCERNABLE MARKER FOR POWER INJECTABLE VASCULAR ACCESS PORT

(75) Inventors: Marshall Kerr, Carlsbad, CA (US); Alain Rosier, Neuchatel (CH)

(73) Assignee: PFM Medical, Inc., Carlsbad, CA (US)

( * ) Notice: Subject to any disclaimer, the term of this patent is extended or adjusted under 35 U.S.C. 154(b) by 1099 days.

(21) Appl. No.: 12/700,695

(22) Filed: Feb. 4, 2010

(65) Prior Publication Data
US 2010/0198057 A1 Aug. 5, 2010

Related U.S. Application Data

(60) Provisional application No. 61/149,967, filed on Feb. 4, 2009.

(51) Int. Cl.
*A61M 39/02* (2006.01)
*A61B 6/12* (2006.01)

(52) U.S. Cl.
CPC .......... *A61B 6/12* (2013.01); *A61M 39/0208* (2013.01); *A61M 2039/0238* (2013.01); *A61M 2205/6036* (2013.01)

(58) Field of Classification Search
CPC .............. A61M 31/00; A61M 2205/32; A61M 2039/0238
USPC ........ 604/288.01, 288.02, 116, 506, 264, 65; 604/189, 890.1; 600/424; 382/132, 128; 705/3
See application file for complete search history.

(56) References Cited

U.S. PATENT DOCUMENTS

| | | | | |
|---|---|---|---|---|
| 4,854,324 A * | 8/1989 | Hirschman et al. | .......... | 600/432 |
| 6,287,293 B1 * | 9/2001 | Jones et al. | ................ | 604/891.1 |
| 7,785,302 B2 * | 8/2010 | Powers | .................... | 604/288.02 |
| 8,442,623 B2 * | 5/2013 | Nicoson et al. | ............. | 600/431 |
| 9,101,344 B2 * | 8/2015 | Larson | .................. | A61B 18/02 |
| 2002/0087115 A1 * | 7/2002 | Hartlaub | ........................ | 604/65 |
| 2006/0239411 A1 * | 10/2006 | Schutz | ........................ | 378/165 |
| 2006/0264898 A1 * | 11/2006 | Beasley et al. | ............... | 604/506 |
| 2008/0228164 A1 * | 9/2008 | Nicoson | .................. | A61B 90/39 604/506 |
| 2008/0273748 A1 * | 11/2008 | Meiring et al. | ............... | 382/100 |
| 2008/0319399 A1 * | 12/2008 | Schweikert | ........ | A61M 39/0208 604/175 |
| 2009/0024098 A1 * | 1/2009 | Bizup | ................ | A61M 39/0208 604/288.02 |
| 2009/0099457 A1 * | 4/2009 | Barnes | .......................... | 600/476 |
| 2009/0227951 A1 * | 9/2009 | Powers | ............. | A61M 39/0208 604/116 |
| 2011/0118677 A1 * | 5/2011 | Wiley | ................ | A61M 39/0208 604/288.01 |
| 2011/0275930 A1 * | 11/2011 | Jho et al. | ....................... | 600/424 |
| 2012/0172711 A1 * | 7/2012 | Kerr | .......................... | A61B 6/12 600/411 |
| 2014/0276740 A1 * | 9/2014 | Larson | .................... | A61B 18/02 606/33 |
| 2015/0327927 A1 * | 11/2015 | Larson | .................... | A61B 18/02 165/11.1 |

* cited by examiner

*Primary Examiner* — Bhisma Mehta
*Assistant Examiner* — Matthew A Engel
(74) *Attorney, Agent, or Firm* — Donn K. Harms

(57) ABSTRACT

An improved injection port for implantation within a patient having an x-ray discernable marker allowing for the determination of a pressure rating for the injection port when so implanted.

3 Claims, 2 Drawing Sheets

X-RAY DISCERNABLE MARKER FOR POWER INJECTABLE VASCULAR ACCESS PORT

This application claims priority to U.S. Provisional Patent Application No. 61/149,967 filed 4 Feb. 2009, which is incorporated herein in its entirety by reference.

FIELD OF THE INVENTION

The disclosed device relates to power-injectable vascular access ports which are implanted in a patient and conventionally employed for powered injection of medicine and medical related injectables such as during an injection of contrast media for a CT scan. More particularly, it relates to such a vascular access port which provides the medical professional a marker which is X-ray discernable thereby providing a means for visual confirmation that the implanted power port itself is rated for powered injection under high pressure.

BACKGROUND OF THE INVENTION

Intravenous therapy or IV therapy is the giving of liquid substances directly into a blood vessel. Such therapy may be intermittent or may be continuous and during the therapy a fluid conduit must be established into the vascular system of the patient and maintained.

The simplest form of intravenous access is a syringe with an attached hypodermic needle. The needle is inserted through the skin into a blood vessel, and the contents of the syringe are injected through the needle into the bloodstream. Since direct injection only allows for the delivery to a patient of a single dose of medication, where prolonged therapy using multiple doses is to the regimen, a more popular mode employs a peripheral IV line consisting of a short catheter (a few centimeters long) inserted through the patient's skin into a sealed engagement with a peripheral vein. A hub in sealed communication with the axial passage of the catheter is engaged on the distal end of the catheter and remains outside the patient's body, usually on the skin surface. In this position the hub can be connected to a syringe or an intravenous infusion line to communicate fluid to the bloodstream of a patient, or capped when not in use. The hub and engaged catheter thus allows for multiple treatments with the same line.

However, on many patients a more direct route to the central veins is required for medication, treatments, and imaging. Conventionally, a central venous line provides access for this purpose and consists of a catheter is inserted into a subclavian, internal jugular, or (less commonly) a femoral vein and advanced toward the heart until it reaches the superior vena cava or right atrium. Because all of these veins are larger than peripheral veins, central lines can be employed to deliver a much higher volume of fluid and can also have multiple lumens feeding the central line.

Implantable ports are a type of central venous line which does not employ an external connector positioned outside the patient's body. Instead, such implantable ports have a small reservoir which is covered with a flexible cover and the entire device is implanted under the skin of the patient. Once so implanted, medication is administered to the patient thereafter by placing a small huber needle through their skin, piercing the flexible cover of the port, and injecting the medication directly into the reservoir under the flexible cover. When the needle is withdrawn, the reservoir cover is formed of a material which reseals itself.

Since the implanted port reservoir cover can accept hundreds of needle piercings during its lifetime, it is possible to leave the ports in the patient's body for years. This helps avoid infection by leaving the skin barrier intact and over time is much less painful to the patient since they need not endure pokes and needle sticks and an incision required by exterior mounted ports.

A particular problem occurs for medical professionals when implantable ports are infused using power injection. Such infusions communicate the liquid into the implanted port under high pressure in order to move a large amount of liquid into the body of the patient in a short time. Such powered injection devices can communicate high pressure levels through the cover and into the reservoir of the implanted infusion port. The implanted port therefor must be rated for the anticipated high fluid pressure or a rupture of the port and related serious problems will occur.

Because the implanted port is positioned under the skin of the patient, it cannot be visually inspected during and after use. Consequently, it is hard for medical personnel to ascertain if in fact the implanted port is rated for high pressure and resulting high volume of the anticipated infusion to be given the patient. Hidden from view by the patient skin layer, it is not possible to examine the implanted port prior to use.

However, most medical protocols require two means of ascertaining the implanted port is high-pressure rated prior to using it for that purpose during a subsequent high pressure injection through the cover of the port. Currently, one means to ascertain the port pressure rating is where the patient's chart may be marked with the pressure rating on the hidden port, or the patient may wear an ID bracelet, or other means to denote that the implanted port is rated to the pressure to which it is about to be connected.

However, there is no means for visual confirmation of the implanted and skin-covered port's pressure rating by the medical professional. Consequently, they must depend upon the accurate charting and labeling by themselves and by other workers. With charts and bracelets being known to be less than accurate on occasions, or in cases where a chart indicates one pressure rating and a bracelet indicates another, it would be especially helpful to provide a fail-safe means to ascertain the pressure rating of the implanted port. In cases where the records and charts disagree, such a failsafe means would also prevent needless patient procedures to remove or replace implanted ports when two means of identification cannot be found.

As such, there exists a continual unmet need, for a means for medical professionals to visually identify that an implanted infusion port, hidden by skin and other patient tissue, is actually rated for the high pressure use for which it is about to be employed. Such a means of identification should be easy to employ, and allow for the use of the installed base of medial equipment already in hospitals and medical offices to lower costs and insure widespread easy deployment.

With respect to the above, before explaining at least one preferred embodiment of the invention in detail or in general, it is to be understood that the invention is not limited in its application to the details of construction and to the arrangement of the components or the steps set forth in the following description or illustrated in the drawings. The various apparatus and methods of the invention are capable of other embodiments, and of being practiced and carried out in various ways, all of which will be obvious to those skilled in the art once the information herein is reviewed. Also, it is to be understood that the phraseology and terminology employed herein are for the purpose of description and should not be regarded as limiting.

As a consequence, those skilled in the art will appreciate that the conception upon which this disclosure is based may readily be utilized as a basis for designing new X-ray or fluoroscope discernable markers, allowing for a power and a pressure rating verification of implanted infusion ports and the like, and for carrying out the several purposes of the present disclosed device and method. It is important, therefore, that the embodiments, objects and claims herein, be regarded as including such equivalent construction and methodology insofar as they do not depart from the spirit and scope of the present invention.

SUMMARY OF THE INVENTION

The marker device allowing the identification method herein is employed in combination with an injection port (or portacath) which is a small medical appliance that is conventionally installed beneath the skin. Such ports are designed for implantation under the skin of a patient and the port employs a septum or membrane cover on an upper surface closest to the patient's skin. This cover provides a self-sealing means to communicate with an underlying reservoir and is adapted to be pierced by a needle or other means to communicate medicine and drugs into the underlying reservoir or for the taking of blood samples therefrom on numerous occasions. A catheter or other means for sealed communication of a lumen between a blood vessel and the reservoir connects the reservoir under the septum to an internal blood vessel such as a vein.

The marker device allowing for identification of the implanted port, is engaged to, or within, the implanted port and is formed of a material such as nitenol or tungsten or titanium, which can easily be discerned on a CT scan or X-ray or on a fluoroscope. The marker may be a planar piece of material that is engaged within the interior, or upon the exterior of the implanted port, or it may be a piece of the preferred discernable material which is engaged within the reservoir cavity within the implanted port. Other materials, which will be substantially discernable on an x-ray, may be employed such as ink infused with metallic material such as titanium and which may be imparted to an interior or exterior surface of the implanted port.

In use, for instance during a CT scan where a large volume of liquid is required to be communicated to the port by a power injection under high pressure, the medical professional performing the procedure can first ascertain if the implanted port has the high pressure rating required for the procedure. The user can do so quickly by simply taking a quick X-ray of the patient in the vicinity of the implanted port. If the port is pressure rated for the procedure, the maker which in this case is a triangular shaped marker formed of the material which will show on the X-ray, will be easily discernable on the X-ray as engaged to or within the plastic implanted port. This will provide a visually discernable positive affirmation the port is, or is not pressure rated for the upcoming procedure.

As an additional safety protocol, the software which controls the CT scan or other X-ray procedure may be programmed with image recognition program to be employed prior to the procedure moving forward. In this mode, the scanner or x-ray machine would be adapted to initially seek out the port and identify the marker in an initial scan of the patient before allowing the medical professional to continue with the procedure. Once identified by software adapted to recognize acceptable identifiers engaged to the port, a microprocessor will allow the employment of the next procedural step which would involve a powered injection to be communicated through the cover and into the reservoir of the port under high pressure.

Still further, the markers so engaged to or on the port, may be cross referenced with a database of pressure ratings. This would allow for the employment of multiple ports with higher and lower pressure ratings wherein a triangular shape for example would verify on pressure rating and a rectangular shape would verify a different pressure rating.

The ability to view a maker engaged to or upon the implanted port will thus provide a means to visually discern that an implanted port, hidden under the patient's skin, is rated for the pressure to which it will be exposed in an upcoming procedure.

The foregoing has outlined rather broadly the more pertinent and important features of the device and method herein employing X-ray discernable markers upon or within implantable ports in order that the detailed description of the invention that follows may be better understood so that the present contribution to the art may be more fully appreciated. Additional features of the invention may be described hereinafter which form the subject of the claims of the invention. It should be appreciated by those skilled in the art that the conception and the disclosed specific embodiments may be readily utilized as a basis for modifying or designing other X-ray discernable marking systems for implanted ports for carrying out the same purposes of the present invention. It should also be realized by those skilled in the art that such equivalent constructions and methods do not depart from the spirit and scope of the invention as set forth in the appended claims.

In this respect, before explaining at least one embodiment of the invention in detail, it is to be understood that the invention is not limited in its application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

THE OBJECTS OF THE INVENTION

It is therefore an object of the present invention to provide a visual means to determine if an implanted and skin-covered port, is power-rated for engagement to high pressure.

It is another object of this invention to provide such a device and method that may be easily incorporated into existing implantable ports, and be identified with the installed base of medical equipment at medical facilities.

It is yet another object of this invention, to employ such identifiable pressure rating markers which may be identified by a computer running software adapted to the task and thereby prevent accidental injection in a subsequent step if the proper pressure rating is not discerned.

The foregoing has outlined some of the more pertinent objects of the invention. These objects should be construed to be merely illustrative of some of the more prominent features and applications of the intended invention. Many other beneficial results can be attained by applying the disclosed method and device in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

BRIEF DESCRIPTION OF THE DRAWINGS

The accompanying drawings, which are incorporated in and form a part of this specification, illustrate embodiments of the invention and together with the detailed description, serve to explain the principles of this invention.

DETAILED DESCRIPTION OF THE PREFERRED EMBODIMENTS

Figure 1:
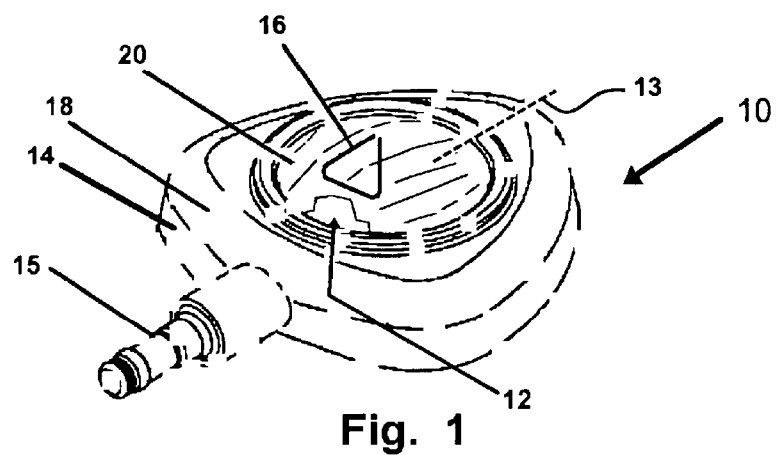
FIG. 1 depicts a perspective view of the device herein engaged to, or floating within an interior cavity or the reservoir of an implanted port shown in dotted line.

Referring now to the drawings 1-3, wherein similar parts of the invention are identified by like reference numerals, the device 10 as shown in FIG. 1 is seen having a marker 16 engaged to or floating within an interior cavity 12 of a port 14 shown in dotted line. The device 10 would be produced in combination with the port 14 and deployed in a conventional sterile container for implantation.

An outlet 15 of the port 14 is engageable to a catheter or other device providing a lumen which is in sealed communication with a blood vessel of the patient. Any such implanted port 14 may employ the device herein by the inclusion of the marker 16 in an engagement to the body 18 of the port 14 or by positioning within an interior cavity 12 of the port 14.

Figure 2:
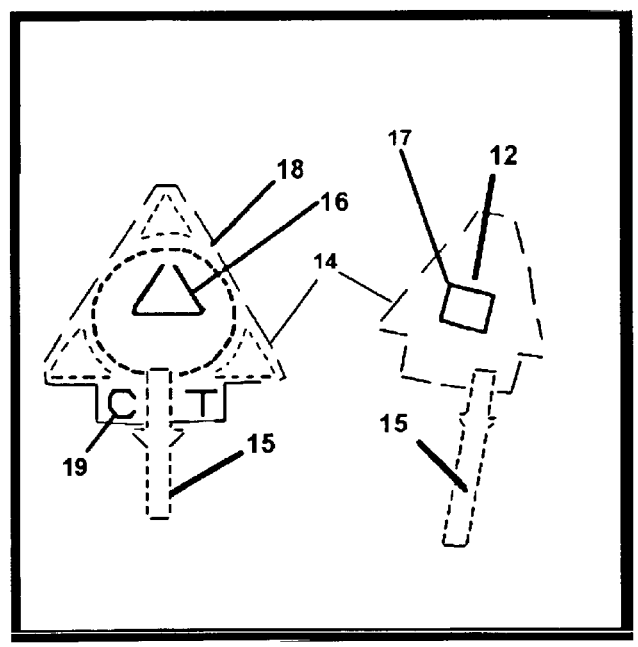
FIG. 2 depicts an X-ray of the device of FIG. 1 wherein the marker is rendered visible by a human or computer with operative recognition software, within the implanted port, and showing the device positioned within a reservoir under the septum.

As noted the marker 16 is best formed of a material that is easily visually discernable by the eye of a viewer of an X-ray as shown in FIG. 2. Such materials may include one or a combination of marker materials from a group including nitenol, tungsten, titanium, or inks containing discernable material which may be printed or adhered to the port 14, or other materials which will easily show on an X-ray.

The marker 16 may be a solid pieced of material or may be painted or appliqued to the port 14. Additionally should the port 14 have multiple pressure ratings for differing procedures, indicia 19 indicating the pressure rating for the port 14 may be included in the marker 16, or the marker 16 itself may be shaped differently such as a triangle marker 16 or a rectangular marker 17 each of which are cross referenced to a specific pressure rating.

Engaged within or upon the port 14, the marker 16 yielding the disclosed device 10 in combination with a port 14, will be clearly visible on an X-ray as shown in FIG. 2. In one mode in FIG. 2 the marker 16 is engaged to the body 18 of the port 14 and in another image in the X-ray the marker 17 is shown floating within an interior cavity 12 below the septum 20 through which a needle penetrates to communicate an injection of a volume of fluid under high pressure to the port 14 in a medical procedure such as a CT scan.

Figure 3:
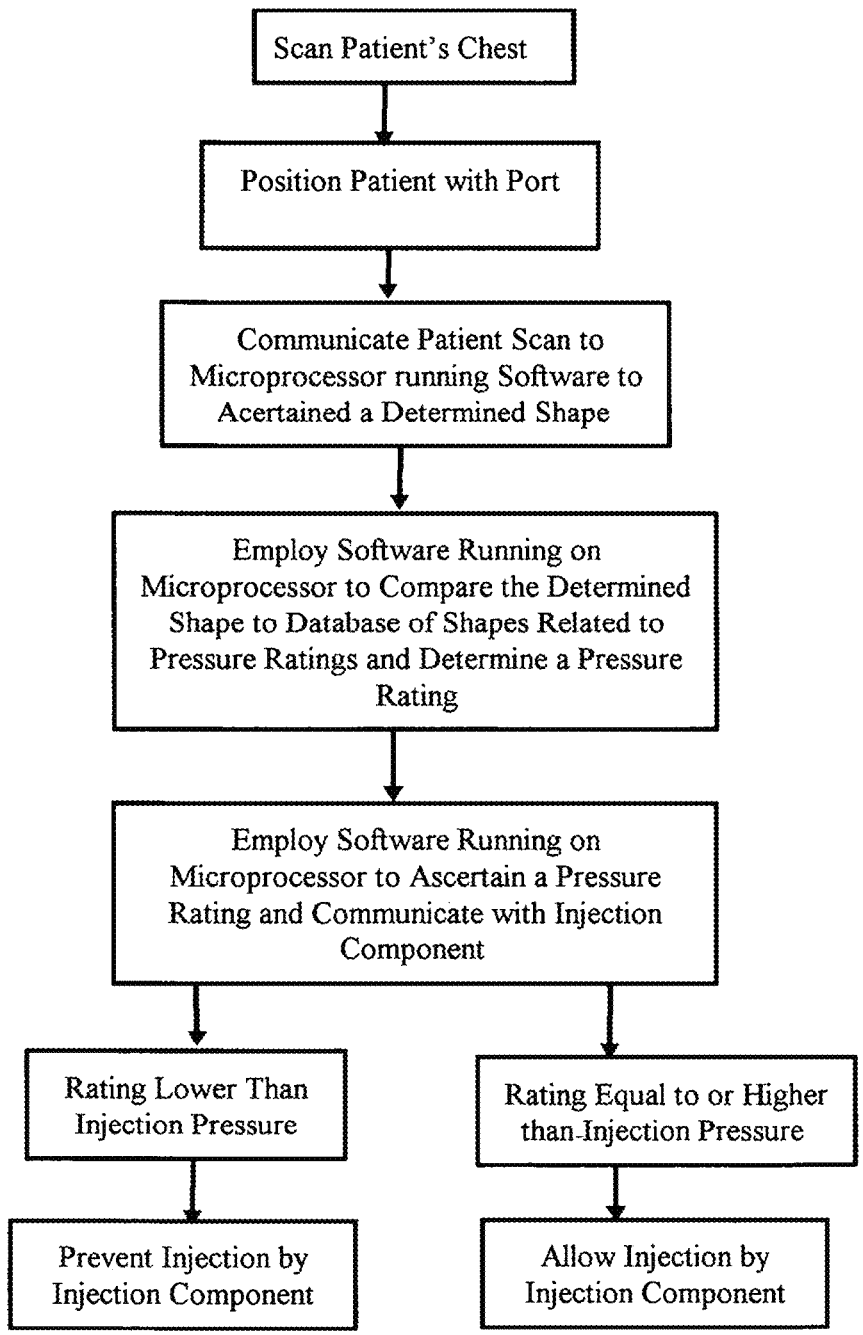
FIG. 3 depicts, graphically, a method of implementation of the device in a method to prevent high pressure injections to ports not recognized as capable of handling the intended pressure.

FIG. 3 depicts an implementation of the device 10 in a method providing a means to prevent high pressure injections to ports not recognized as capable of handling the intended pressure. As noted the software running the CT scanning device, or other X-ray device, may be adapted for use during medical procedures which require a high pressure rated port 14. The software will employ the scanner to run an initial scan of the patient and use image recognition software to ascertain the presence of the marker 16, prior to allowing the technician to inject the port 14 under high pressure in a second step. Because the port 14 is easily visually identifiable for pressure rating based on the marker 16 or 17 discerned, multiple ports 14 with multiple pressure ratings might be used without worry. Since ports 14 which must survive higher pressures generally cost more, the employment of markers 16 or 17 in solid or printed format which provide visual confirmation of the rating of the hidden port 14, will allow for less expensive ports 14 to be employed where subsequent pressures are anticipated to be lower.

If the software mode of the method herein is employed, the CT scanner or other device would in a first step take an initial scan and employ visual recognition software to discern the shape of the marker 16 or 17. In a second step, when only one shape is employed to designate an acceptable pressure-rated port, software running on a microprocessor, will ascertain the presence of the port and the injection would be permitted. If more than one shape of the identifier is employed due to multiple ratings on multiple ports, the software would use the initial scan to ascertain the identifier present, and would then match the ascertained shape of the identifier in the patient, in a relational database with the shape as related to a predetermined pressure rating for ports bearing the recognized identifier. The procedure would only be allowed to proceed to the high pressure injection if the proper pressure rating is discerned from the relation of the identifier with the data regarding it accessed by the software in the identification step.

While all of the fundamental characteristics and features of the disclosed device and method herein have been described herein, with reference to particular embodiments thereof, a latitude of modification, various changes and substitutions are intended in the foregoing disclosure and it will be apparent that in some instance, some features of the invention will be employed without a corresponding use of other features without departing from the scope of the invention as set forth. It should be understood that such substitutions, modifications, and variations may be made by those skilled in the art without departing from the spirit or scope of the invention. Consequently, all such modifications and variations are included within the scope of the invention as defined herein.

What is claimed is:

1. An injection port for long term implantation under a skin of a patient, comprising:
    a body having an interior cavity, said interior cavity communicating into said body and covered by a septum, said interior cavity configured for receiving fluid from an injection from a needle piercing said septum;
    said injection port having a pressure rating for the fluid from said injection into said interior cavity;
    a marker in an engagement with said body, said marker formed of a material which is clearly discernable for a shape in a viewed X-ray of said port;
    said engagement of said marker with said body being said marker floating within said interior cavity; and said shape of said marker in said viewed x-ray corresponds to said pressure rating of said injection port, whereby said pressure rating said injection port can be ascertained without removing said pressure port from under the skin of said patient and said injection port may be left implanted in said patient for weeks and said marker employed for discerning said pressure rating of said pressure port prior to each subsequent one of said injections.

2. The injection port for implantation under the skin of the patient of claim 1 additionally comprising:

said material forming said marker is formed from one or a combination of marker materials from a group of marker materials including nitenol, tungsten, titanium, and inks containing x-ray discernable material which are adherable to said port.

3. The injection port for implantation under the skin of the patient of claim 1 additionally comprising:

indicia positioned upon said injection port, said indicia corresponding to said pressure rating, said indicia formed of a material which is visible in said viewed x-ray.

\* \* \* \* \*